United States Patent [19]

Tyihák et al.

[11] Patent Number: 4,591,524
[45] Date of Patent: May 27, 1986

[54] CHROMATOGRAPHIC SHEET OF LAYER FOR PRESSURIZED LAYER CHROMATOGRAPHIC APPARATUS

[76] Inventors: Ernö Tyihák, Zápor u.59. 1032, Budapest; Emil Mincsovics, Vásárhelyi K.tér 4. 2000, Szentendre; József Knoll, Jászai M.tér 4/b 1137, Budapest; Sándor Zoltán, Sárköz u.7/a 1142, Budapest; István Lak, Gellérthegy u.3. 1016, Budapest; Péter Tétényi, Népstadion u.9. 1143, Budapest; Huba Kalász, Hevesi Gy.u.95.1157, Budapest; János Nagy, Jókai u.2. 2000, Szentendre, all of Hungary

[21] Appl. No.: 285,090

[22] PCT Filed: Dec. 5, 1980

[86] PCT No.: PCT/HU80/00006
§ 371 Date: Jul. 15, 1981
§ 102(e) Date: Jul. 15, 1981

[87] PCT Pub. No.: WO81/01746
PCT Pub. Date: Jun. 25, 1981

[30] Foreign Application Priority Data
Jun. 12, 1979 [HU] Hungary ............... CI 1995

[51] Int. Cl.$^4$ .......................... B32B 3/02; B32B 3/30; G01N 31/08
[52] U.S. Cl. ................... 428/167; 210/198.2; 210/198.3; 210/656; 210/658; 428/136; 428/137; 428/138; 428/157; 428/173; 428/192; 428/194; 428/200; 428/210; 428/325
[58] Field of Search ............... 428/131, 136, 137, 138, 428/193, 194, 195, 172, 173, 81, 157, 167–169, 192, 200, 210, 325, 364; 210/198.2, 198.3, 656, 658

[56] References Cited

U.S. PATENT DOCUMENTS 3,878,100  4/1975  Bixler ............... 210/198.3
4,126,554  11/1978  Rainin ............... 210/658

Primary Examiner—Bruce H. Hess
Attorney, Agent, or Firm—Anthony H. Handal

[57] ABSTRACT

An adsorbent layer (stationary phase) for a pressurized layer chromatographic apparatus, for the development of linear chromatogram, is sealed at the edges by impregnation. For the purpose of solvent control some of the adsorbent material is removed in one or several zones of the adsorbent layer near the place of solvent admission, or one or several baffle plates or wires are arranged behind the place(s) of sample application, or if necessary, the adsorbent layer is provided with a conventionally formed concentration zone in the area of the solvent admission. As a result of the impregnation, the migrating solvent composite does not escape at the edges of the adsorbent layer according to the invention in case of overpressure. As a result of the removal of adsorbent material, or the arrangement of baffles or wires, or the application of a concentration zone, the solvent migrates with a straight-line front.

18 Claims, 5 Drawing Figures

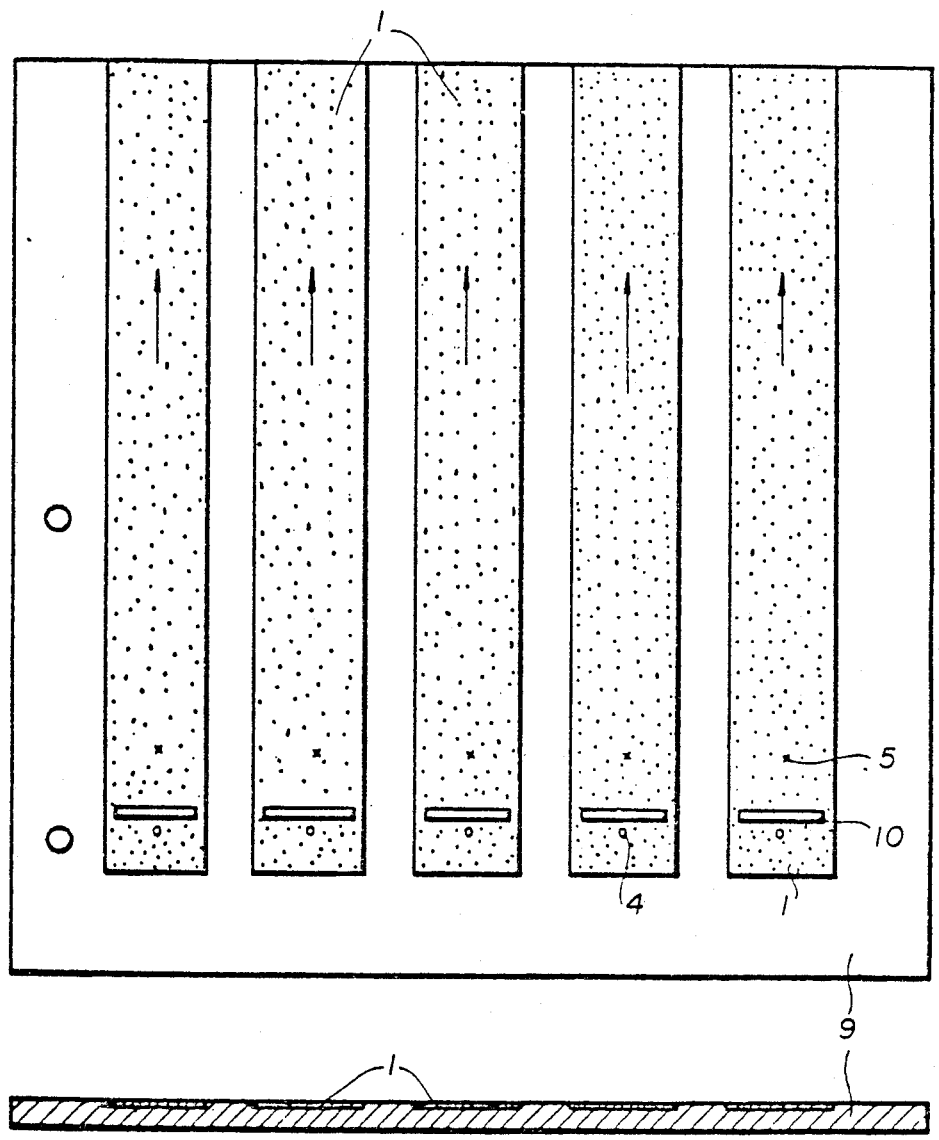

CHROMATOGRAPHIC SHEET OF LAYER FOR PRESSURIZED LAYER CHROMATOGRAPHIC APPARATUS

BACKGROUND OF THE INVENTION

The invention relates to a specially prepared chromatographic sheet with adsorbent layer favorably used in pressurized layer chromatographic apparatuses, for the development of linear chromatograms.

Layer chromatography, which is liquid chromatography in a planar arrangement, is a method whereby a mobile phase (the solvent composite) travels on the stationary phase (the adsorbent layer) and carries one or several substances at varying speeds. By the layer chromatographic process, chemical compounds are preferentially adsorbed in an increasing molecular weight sequence onto the solid adsorbent material (the stationary phase). This adsorption is made possible by the solvent (the mobile phase) eluting adsorbed materials from the adsorbent. The distribution of the travelling compounds along the path of the solvent allows the separation of the chemical compounds.

One drawback of classical layer chromatography is the long developing time. Another drawback is that, due to the short length of the adsorbent layer, the separation is not perfect and the theoretical number of plates is limited.

Significant progress was made by the development of high-performance thin-layer chromatography (HPTLC) (see A. Zkatkis and R. E. Kaiser: High Performance Thin-Layer Chromatography, Elsevier, 1977), which, contrary to the classical layer chromatography, results in better dissolution in shorter developing times and shorter distances.

However, the most up-to-date technique is the so-called pressurized (sealed) layer chromatography (Hungarian Patent No. 173,749) which is realizable equally well on thin and thick layers, and provides the fastest separation. The essential step in the technique of pressurized layer chromatography is the application of an overpressure in a closed system to achieve a flow velocity of the solvent (mobile phase) over the adsorbent layer (stationary phase). The adsorbent layer is completely covered suitably with elastic foil, which is pressed in a cushion-like manner against the adsorbent layer by the application of external pressure. The cushion pressure (2-10 bar) should always be higher than the flow pressure (1-8 bar) of the solvent composite. In this so-called pressurized ultramicron chamber a separation can be attained within a very short time (1-10 minutes) which is better than that attainable in the earlier known chromatographic methods utilizing a planar arrangement. An apparatus was constructed for the development of both the concentric and linear chromatograms.

However, the following fundamental problems exist in the linear alternative of the pressurized layer chromatography as a result of the overpressure: (1) the solvent composite escapes at the edges of the adsorbent layer and (2) the front of the solvent flow is not straight, but rather is concentric, semicircular, or arc-shaped following solvent admission, e.g., in case of solvent admission at one point.

SUMMARY OF THE INVENTION

In working out the invention, the aim was to develop a chromatographic sheet with adsorbent layer (stationary phase) applicable in the pressurized layer chromatographic apparatus, which would eliminate the escape of the flowing solvent composite (mobile phase) at the edges of the adsorbent layer, and on which the solvent composite would travel with a straight front.

The invention is based on the recognition that if the adsorbent layer is suitably sealed at its edges, then the solvent cannot escape when overpressure is applied.

Furthermore, the invention is based on the recognition that if the adsorbent layer at and/or near the place of solvent admission is removed from the carrier plate in one or several thin zones, or a thin baffle plate(s) or wire(s) is placed directly in front of the place of solvent admission, i.e., if a minisolvent composite chamber is formed, then the solvent composite will migrate with straight-line front.

BRIEF DESCRIPTION OF THE DRAWINGS

The preferred embodiments of the present invention are described with reference to the following figures:

FIG. 5 is a schematic diagram of the top view of another embodiment according to the present invention, including separated adsorbent layers and synthetic foil bars.

DESCRIPTION OF THE INVENTION

Sealing of the adsorbent layer according to the invention is realized by impregnation, or by shrinking the adsorbent layer by the addition of powdered glass, whereby varying shrinkage conditions are ensured at the edges of the adsorbent layer and in the chromatographic field, or by forming one or several parallel grooves in the carrier plate and placing the adsorbent layers into the grooves, whereby the carrier plate itself seals the edges, or when a ceramic plate is employed, by glazing its edges.

The impregnating or glazing materials should (1) be insoluble in the solvent used for the chromatography, (2) be unaltered as a result of the overpressure of the solvent composite and under the given temperature conditions and (3) not react chemically with either the adsorbent layer or the foil that seals the adsorbent layer from above.

Preferably paraffin or synthetic solutions, or suspensions, water-glass (sodium silicate) may be used as the impregnating material. The edges of the ceramic plates may be coated with white tin-lead glaze. In the case of shrinkage by the addition of powdered glass, varying qualities of powdered glass are used on the edges, but the use of other additives on the edges is also suitable.

Figure 1:
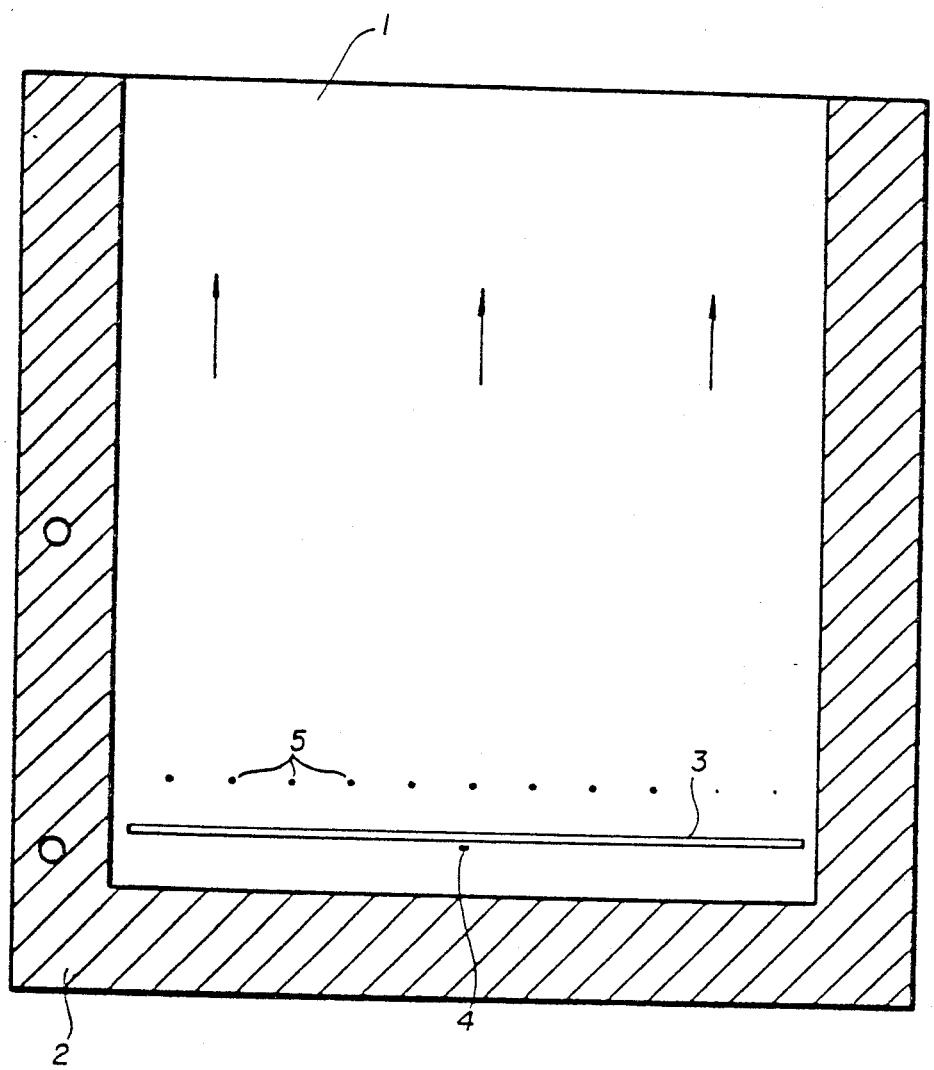
FIG. 1 is a schematic diagram of the top view of a preferred embodiment according to the present invention, including impregnated edges and a steel wire.
Figure 2:
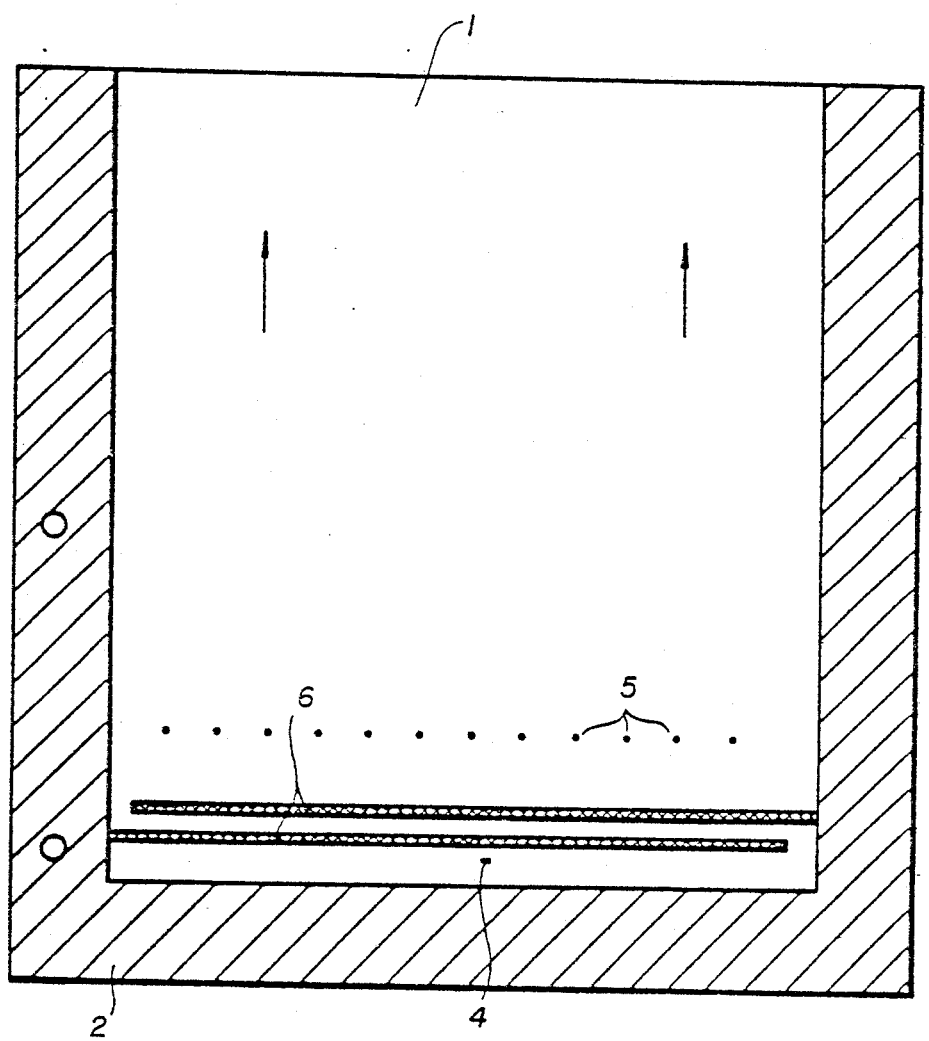
FIG. 2 is a schematic diagram of the top view of another embodiment according to the present invention, including impregnated edges and grooves for solvent control.
Figure 3:
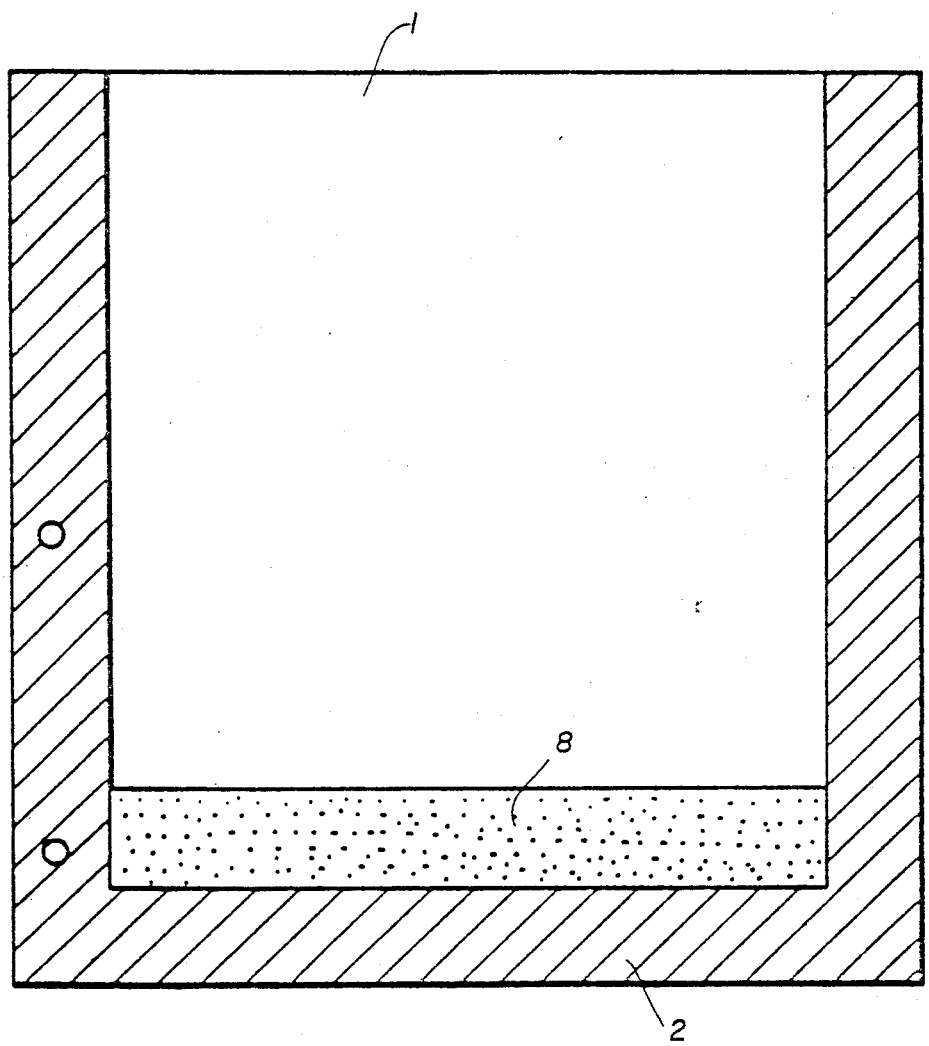
FIG. 3 is a schematic diagram of the top view of another embodiment according to the present invention, including impregnated edges and a concentration zone.
Figure 4:
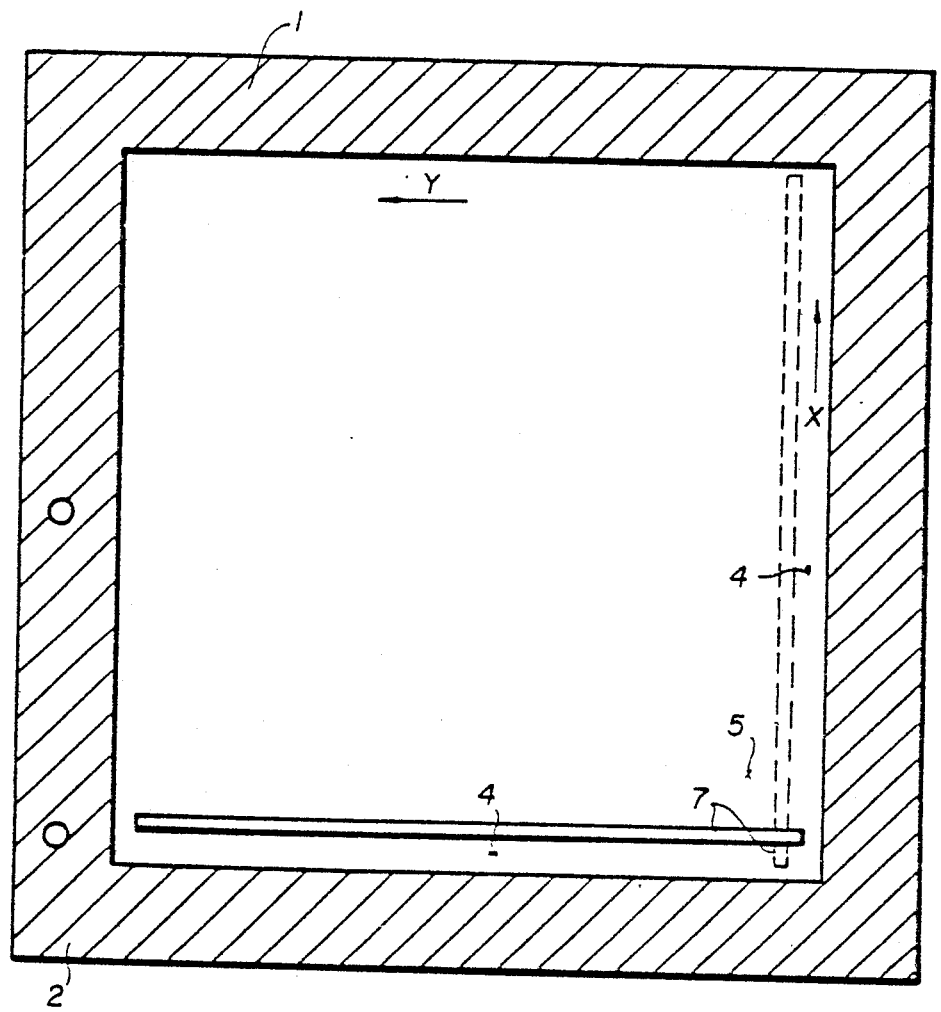
FIG. 4 is a schematic diagram of the top view of another embodiment according to the present invention, including impregnated edges and synthetic foil bars for creating two-dimensional chromatograms.

For one-dimensional development, it is sufficient to seal the adsorbent layer on the two sides parallel to the direction of solvent migration and on the third side opposing this flow (as shown in FIGS. 1–3). For two-dimensional development, however, it is necessary to seal the adsorbent layer on all four sides (as shown in FIG. 4). For the two-directional, linear development with intermediate solvent admission, it is sufficient to seal the two sides opposing the two directions of solvent migration, suitably the longer sides of the adsorbent layer.

The thickness of the sealing layer (e.g., foil) may vary between 0.05 and 3 cm. Most favorable is a thickness of 1 cm or less. The length of the sealing layer is the same as that of the chromatographic plate.

Referring now to FIG. 1, the straight-line front of the migrating solvent composite according to the invention is ensured by the following technique: The adsorbent layer 1 is removed in a width of 0.1–0.5 mm in one or several zones 3 at or near the place of solvent admission 4 and in front of the places of sample application 5 so that this zone 3 of the carrier plate is free of adsorbent. The maximum length of the thusly formed grooves 3 is the same as the length of that portion of the adsorbent layer 1 retained after the edges 2 are coated, but is preferably shorter by 1–20 mm on both sides (as shown in FIG. 1). The grooves 6 may be displaced relative to each other (as shown in FIG. 2). The maximum depth of the grooves should not exceed the thickness of the adsorbent layer. The number of grooves may vary preferably between 1 and 4. In the process according to the invention, 0.05–1.0 mm diameter wire or wires, or baffle plates can be arranged behind the place or places of sample application. The maximum length of the baffle plates or wires after coating of the edges is equal to the length of the retained adsorbent layer, but is preferably shorter by 1–20 mm on both sides. The baffle plates or wires can be displaced in relation to each other. Their number is preferably 1–4. Preferably a gapless synthetic plate is used, fixed by glazing to the adsorbent layer.

A so-called "concentration zone" 8 (see FIG. 3) can also be formed on the solvent admission part of the adsorbent layer formed as described above, which means that a zone of another layer is applied on the adsorbent layer. The material of this applied layer may be, for instance, siliceous earth powdered glass, or synthetic powder, or cellite, i.e., carriers rather than adsorbents used for separation (e.g. aluminum oxide, silica gel), but occasionally highly porous silica gel of a wide pore range is useable against the low-porosity, fine-grained adsorbent layer 1. The double layer formed in this way facilitates the spread of the solvent onto the sample.

Preferably fine-grained (particle diameter 0.5–10 $\mu$m) or normal-grained (particle diameter 10–40 $\mu$m) adsorbent material can be used for the chromatographic layer 1 (stationary phase) according to the invention. Any adsorbent layer available in the art can be used for the pressurized (sealed) layer chromatography according to the invention. However the adsorbent layer may be prepared domestically, too.

The migrating solvent composite does not escape on the edges 2 of the adsorbent layer according to the invention in the case of overpressure and it migrates with a straight-line front.

FIG. 4 depicts a chromatographic plate according to a two-dimensional embodiment of the present invention comprising adsorbent layer 1, impregnated edges 2, two places of solvent admission 4, and two synthetic foil plates 7, at right angles, for controlling the spread of solvent. The solvent migrates in two directions indicated by arrows x and y, and the sample is applied at point 5.

FIG. 5 depicts another embodiment of the present invention wherein the adsorbent material 1 is applied to grooves in a carrier plate 9. For solvent control, each strip of adsorbent material is provided with a synthetic foil plate 7 situated between the place of solvent admission 4 and the place of sample application 5.

PREFERRED EMBODIMENTS OF THE INVENTION

The invention is illustrated with the following examples:

EXAMPLE 1

110 ml of 0.85% watery solution of relatively highly polymerized homopolymeric polyacrylamide is added to 32 g of silica gel powder of 4–8 $\mu$m grain size and 60 Å inside diameter. After thorough mixing the 0.25-mm-thick suspension is applied on degreased, 20×20 cm, 1.5-mm-thick glass panels according to the known method. The layers after drying at room temperature are of good mechanical strength even after activation.

The edges of the adsorbent layer, obtained in this manner and subsequently activated, are impregnated in a width of 10 mm, by dipping three sides of the adsorbent layer into commercial paraffin melted at 130° C.

For directing the solvent, 0.2-mm-diameter steel wire is placed in front of the place of solvent admission in groove 3 as shown in FIG. 1. With the use of methylene chloride solvent, authentic dye materials (butter-yellow, Sudan G, and indophenol) can be well separated in the so-called pressurized ultramicron chamber at 1.0 MPa cushion pressure, with 10 minute development time, in a distance of 15 cm.

EXAMPLE 2

The procedure is the same as in Example 1, but in place of 32 g of silica gel powder, 30 g of neutral aluminum oxide of 15–20 $\mu$m grain size is used, applied in a layer 0.3 mm thick.

EXAMPLE 3

100 ml of 1.8% watery solution of the polymerisate of an acrylamide and acrylic acid anionic mixture of low polymerization degree is added to silica gel powder of 4–5 gm grain size and 60 Å inside diameter. After thorough mixing the suspension is applied in a layer 0.3 mm thick onto a 20×40 cm, 0.4-mm-thick sheet of polyterephthalate foil. The layers after drying at 75° C. have adequate strength even after activation. Immediately after the application and before the previously described drying, a 2-mm-wide, 0.3-mm-thick, and 185-mm-long plate of polyteraphthalate foil is placed in front of the intended place of solvent admission, 15 mm from the anticipated odd edge of the impregnated portion of adsorbent layer and equidistant from the other two edges to be impregnated (for a schematic diagram see FIG. 1). This thin plate sticks into the layer during the drying process and is intended to control the solvent upon its admission.

The edges of the dried adsorbent layer obtained in this manner and provided with a control plate (foil) are impregnated by dipping into the 1.5% watery solution of highly polymerized, nonionic polyacrylamide homopolymerism to a width of 5 mm and dried at room temperature.

On the thusly formed adsorbent layer Digital glycosides were effectively separated in a linear pressurized ultramicron chamber, with the use of butanon-2 developer in a distance of 35 cm, at 1.0 MPa cushion pressure, in 18.5 minutes.

EXAMPLE 4

The procedure is the same as in Example 2, but two grooves, each 3 mm wide, are formed in the adsorbent layer for control of the solvent migration (see schematic diagram in FIG. 2).

EXAMPLE 5

100 ml of 2% watery solution of polyvinyl-acetate is added to 26 g of silica gel powder of 8–10 μm grain size and 60 Å inside diameter. Simultaneously 30 ml of 2% watery polyvinyl-acetate suspension is added to 8 g of siliceous earth of 10–20 μm grain size. The two systems are homogenized in separate electric homogenizers for 1 minute, then the obtained two suspensions are poured into two troughs separated proportionally in space and length, and applied to 0.2-mm-thick, 20×20 cm pieces of aluminum foil in the usual way. Thus, a 0.25-mm-thick, coupled, two-zone adsorbent layer is obtained, where the width of the inactive zone 8 (according to the separation of the trough in space and length) is 40 mm (see FIG. 3).

Before the adsorbent layer is dried and immediately after it is applied, a 0.3-mm-thick, 1-mm-wide, 160-mm-long polyterephthalate plate is placed in front of the intended place of solvent admission 15 mm from the odd impregnated edge of the adsorbent layer from the direction of the inactive adsorbent zone 8 and equidistant from the other two, parallel edges to be impregnated for the purpose of the subsequent solvent control.

Then the layer is dried, and possibly activated.

Impregnation of the adsorbent layer's edge in this case was performed as described in Example 2.

On the thusly formed layer provided with the so-called concentration zone 8, the components (sesquiterpenoids) of the volatile oil samples obtained from the influorescence of the *Matricaria chamonmilla* L. by steam distillation were effectively separated in a linear pressurized chamber with benzene as solvent, at 0.7 MPa cushion pressure, with 20 ml/h solvent volumetric velocity, in a distance of 16 cm, in 12 minutes.

EXAMPLE 6

The procedure is the same as in Example 4, but 7 g of cellite powder of 10–20 μm grain size is used instead of the 8 g of siliceous earth.

EXAMPLE 7

36 g of magnesium-silicate powder of 6–10 μm grain size and 110 g of 6°Be sodium silicate watery solution is homogenized in an electric stuff-crusher, and then applied by the usual method on a suitably cleaned, 1.5-mm-thick glass panel. The plates are stored in a chamber of 75% relative moisture content for 2.5 hours, then removed and dried at room temperature. Thus, an adequately stable adsorbent layer is obtained.

The edges of the plates prepared in this manner are impregnated as described in Example 1, and can be used similarly for the effective separation of dye materials.

EXAMPLE 8

The procedure is the same as described in Example 3, except that the two opposite long edges of the adsorbent layer are impregnated before drying by dipping the edge into a 1.5% watery solution of the highly polymerized nonionic polyacrylamide homopolymerism. Also a 1-mm-thick groove is made in the center of the adsorbent layer at the intended place of solvent admission for the subsequent solvent control and two-directional development, then the layer is dried and used for development.

EXAMPLE 9

The procedure is the same as described in Example 7, except that the adsorbent layer is made suitable for two-dimensional development by impregnating it on the fourth side and well after the one-dimensional development, and the solvent control is provided as shown in FIG. 4.

EXAMPLE 10

Five grooves of 0.3 mm depth are formed in a 20×20 cm, 2-mm-thick aluminum plate, into which paste made of polyamide 11 powder of 8–10 μm grain size is applied (25 g of polyamide powder is mixed in 100 ml of 1.5% watery polyvinyl-acetate solution and then homogenized for 1 minute). 15-mm-wide barriers on the edges of the adsorbent layer and 20-mm-wide barriers on the side opposite the direction of solvent flow are formed, while the barriers separating the grooves from each other are formed into smooth surfaces 10 mm wide. In order to ensure a straightline front for the solvent, 16×3×0.3 mm sheets of synthetic foil 7 (polyethylene) are arranged in front of the five solvent admission openings 4, as shown in FIG. 5. The places of sample application 5 are 12 mm from the solvent admission openings 4.

EXAMPLE 11

The procedure is the same as in Example 1, but the applied silica gel contains manganese-activated zinc silicate as fluorescent material.

What we claim is:

1. A chromatographic sheet for pressurized layer chromatography comprising:
   (a) a carrier plate;
   (b) an adsorbent layer of material applied to said carrier plate;
   (c) at least one place on said chromatographic sheet for the admission of solvent;
   (d) at least one place on said chromatographic sheet for the application of sample;
   (e) a plurality of barriers for preventing the escape of said solvent from said chromatographic sheet by sealing the adsorbent layer on at least two edges, and further comprising a linear channel-defining structure for ensuring that the front of migration of said solvent is a straight line.

2. A chromatographic sheet as in claim 1, wherein said plurality of barriers are produced by impregnation of at least two edges of said adsorbent layer by impregnating material.

3. A chromatographic sheet as in claim 2, wherein said impregnating material is paraffin.

4. A chromatographic sheet as in claim 2, wherein said impregnating material is sodium silicate.

5. A chromatographic sheet as in claim 1, wherein said plurality of barriers are produced by shrinkage of said adsorbent layer after the addition of an additive to at least two edges of said adsorbent layer, the shrinkage of the edges with additive of said adsorbent layer being different from the shrinkage of the portion of said adsorbent layer that has no such additives.

6. A chromatographic sheet as in claim 5, wherein said additive is powdered glass.

7. A chromatographic sheet as in claim 1, wherein said carrier plate comprises parallel grooves and said adsorbent layer is applied to said grooves only, whereby said carrier plate seals all of the edges of said adsorbent layer.

8. A chromatographic sheet as in claim 7, wherein said carrier plate is made of ceramic and the edges of said ceramic plate are glazed.

9. A chromatographic sheet as in claim 8, wherein the edges of said ceramic plate are coated with white tin-lead glaze.

10. A chromatographic sheet as in claim 1, wherein said linear channel-defining structure comprises at least one groove formed between said place of solvent admission and said place of sample application by the removal of material from said adsorbent layer, said groove being straight and perpendicular to the direction of migration of said solvent.

11. A chromatographic sheet as in claim 10, wherein the number of said grooves is greater than one and said grooves are displaced relative to one another along the axis perpendicular to the direction of migration of said solvent.

12. A chromatographic sheet as in claim 10, wherein the number of said impregnated edges is at least three, these three being the two edges lying substantially parallel to the direction of migration of said solvent and the edge closest to said place of solvent admission, and said linear channel-defining structure comprises a concentration zone formed by applying a layer of carrier material on said adsorbent layer, said concentration zone having an upper boundary that is straight and perpendicular to the direction of migration of said solvent and that is located between said place of solvent admission and said place of sample application, and having a lower and two side boundaries coterminous with the boundaries of said impregnated edges.

13. A chromatographic sheet according to claim 12, wherein said carrier material is siliceous earth.

14. A chromatographic sheet as in claim 12, wherein said carrier material is powdered glass.

15. A chromatographic sheet as in claim 1, wherein said linear channel-defining structure comprises at least one baffle plate positioned between said place of solvent admission and said place of sample application and embedded in said adsorbent layer, said baffle plate being straight and perpendicular to the direction of migration of said solvent.

16. A chromatographic sheet as in claim 15, wherein the number of said baffle plates is greater than one and said baffle plates are displaced relative to one another along the axis perpendicular to the direction of migration of said solvent.

17. A chromatogrpahic sheet as in claim 14, wherein said linear channel-defining structure comprises at least one wire positioned between said place of solvent admission and said place of sample application and embedded in said adsorbent layer, said wire being straight and perpendicular to the direction of migration of said solvent.

18. A chromatographic sheet as in claim 17, wherein the number of said wires is greater than one and said wires are displaced relative to one another along the axis perpendicular to the direction of migration of said solvent.

* * * * *